United States Patent [19]
Kihara

[11] Patent Number: 5,505,541
[45] Date of Patent: Apr. 9, 1996

[54] STRUCTURE FOR MOUNTING AN AGITATING APPARATUS FOR A DIGESTION TANK

[75] Inventor: Yasuhiko Kihara, Kawasaki, Japan

[73] Assignee: NKK Corporation, Tokyo, Japan

[21] Appl. No.: 312,459

[22] Filed: Sep. 26, 1994

[30] Foreign Application Priority Data

Apr. 28, 1994 [JP] Japan ................... 6-091937

[51] Int. Cl.⁶ .................................................. B01F 5/12
[52] U.S. Cl. ...................................... 366/264; 366/286
[58] Field of Search .................................. 366/262–264, 366/266, 285, 286, 261, 330.1, 347; 261/84, 91, 119.1; 415/221

[56] References Cited

U.S. PATENT DOCUMENTS

| | | | |
|---|---|---|---|
| 2,090,384 | 8/1937 | Durdin, III | 261/91 X |
| 2,186,371 | 1/1940 | Durdin, Jr. | 261/91 X |
| 2,647,733 | 8/1953 | Knowles et al. | 366/286 |
| 4,030,859 | 6/1977 | Henegar | 261/91 X |

FOREIGN PATENT DOCUMENTS

544784  8/1957  Canada ................... 366/262

*Primary Examiner*—Charles E. Cooley
*Attorney, Agent, or Firm*—Frishauf, Holtz, Goodman, Langer & Chick

[57] ABSTRACT

An agitating apparatus for a digestion tank includes a draft tube having two open ends. The draft tube is fixed in an upright direction in a digestion tank such that one open end thereof is submerged in sludge in the digestion tank. A watertight pipe is mounted in an outer wall of the digestion tank to be just above the draft tube such that the watertight pipe has an axis thereof aligned with an axis of the draft tube. An upper end of the watertight pipe protrudes outside of the outer wall of the digestion tank, a lower portion of the watertight pipe protrudes into an upper space of the digestion tank and a lower end of the watertight pipe is spaced apart from the draft tube. The agitating apparatus also includes a cover removably attached to the upper end of the watertight pipe. A watertight connection connects the draft tube and the watertight pipe to each other. An underwater agitator is inserted through the watertight pipe and is disposed in the draft tube. The underwater agitator is extractable through the watertight pipe.

10 Claims, 6 Drawing Sheets

STRUCTURE FOR MOUNTING AN AGITATING APPARATUS FOR A DIGESTION TANK

BACKGROUND OF THE INVENTION

1. Field of the Invention

The present invention relates to an agitating apparatus for an anaerobic digestion tank of sludge.

2. Description of the Related Arts

Figure 5:
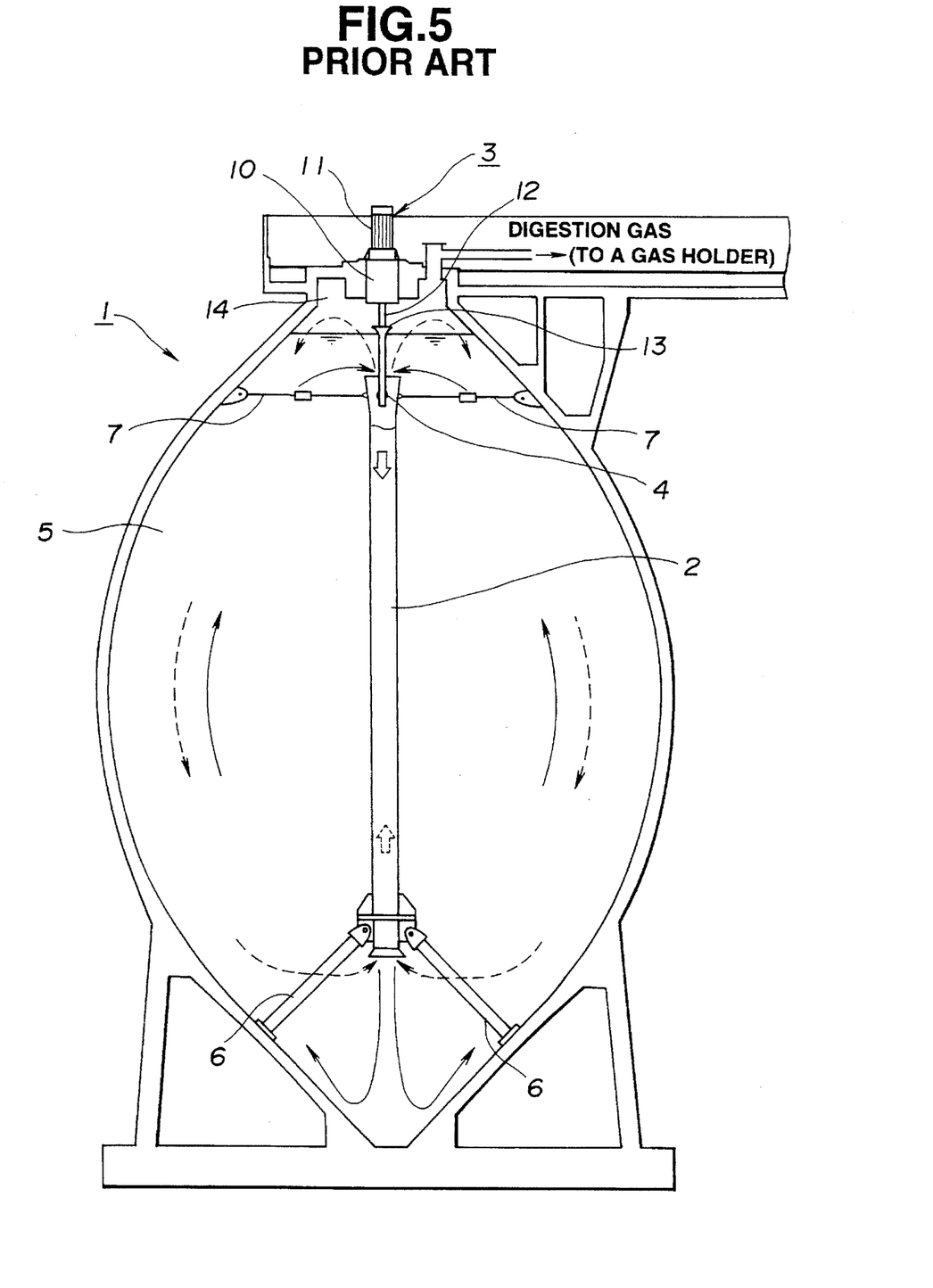
FIG. 5 is a longitudinal sectional view showing an example of a digestion tank of the prior art.
Figure 6:
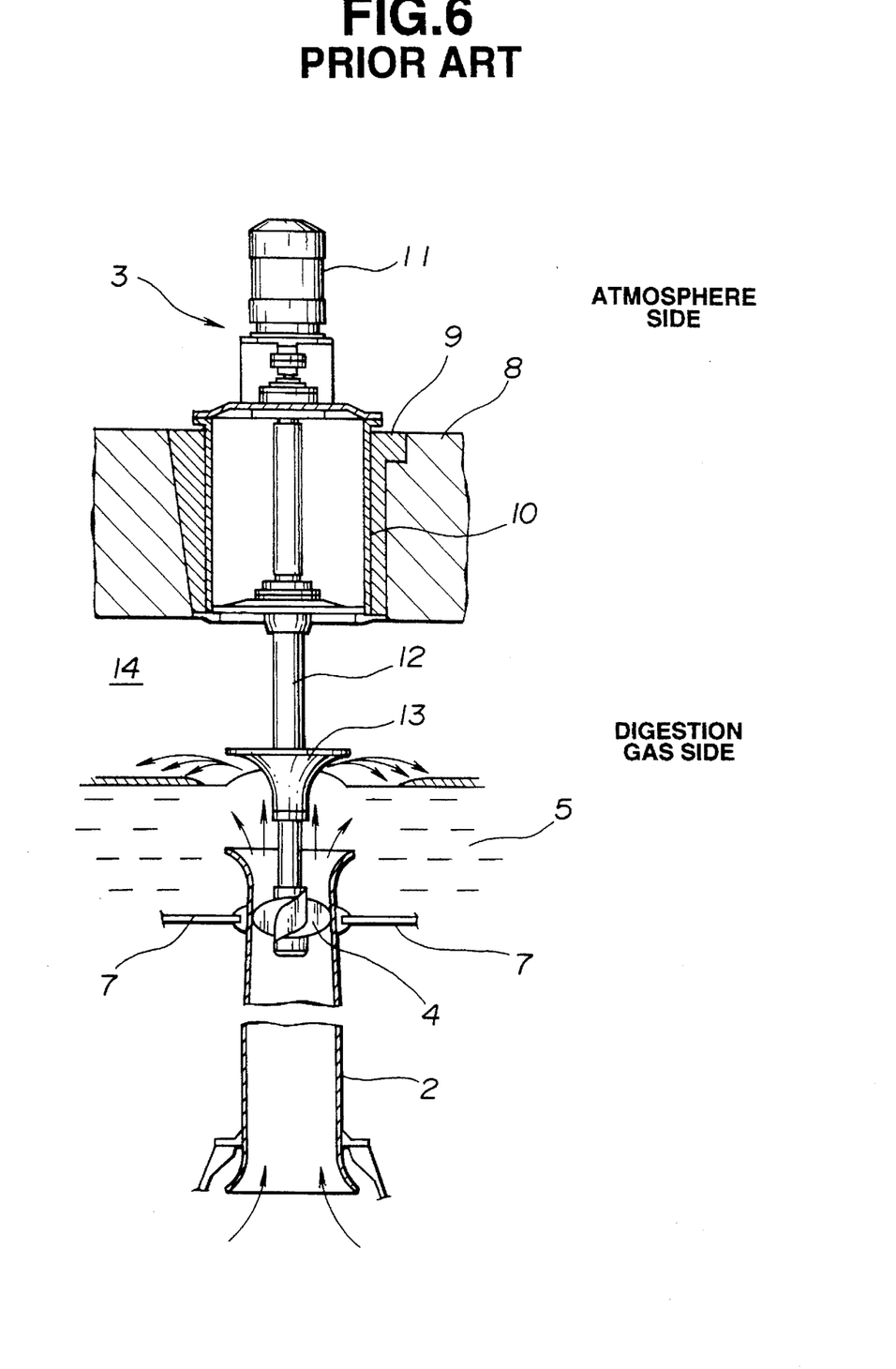
FIG. 6 is a longitudinal sectional view showing, in detail, the mechanical type agitating apparatus of the example of FIG. 5 in an enlarged scale.

FIG. 5 is a longitudinal sectional view showing an entire construction of one example of a digestion tank to be used for an anaerobic sludge treatment of the prior art, as disclosed in Japanese patent examined application No. 46654/84 and FIG. 6 is a longitudinal sectional view showing the details of the mechanical agitating apparatus in an enlarged scale.

This digestion tank 1 is equipped therein with a draft tube 2 which is erected upright so that it can be submerged in the inside sludge. A screw 4 of an agitator 3 is inserted into the draft tube 2 from the upper open end so that downward (as indicated by solid arrows in FIG. 5) or upward (as indicated by broken arrows in FIG. 6) flows can be generated in tile draft tube 2 by rotating tile screw 4 which generates circulation flows in the tank by forced convection to agitate the sludge 5 as a whole. In other words, the draft tube 2 and the screw 4 function like a vertical axial flow pump using the screw 4 as its impeller and the draft tube 2 as its casing.

More specifically, the draft tube 2 has its lower portion fixed in the inner wall of the lower portion of the digestion tank 1 through a plurality of legs 6, as shown in FIG. 5, and its upper portion fixed in the inner wall of the upper portion of the digestion tank 1 through tie rods 7. As a result, the draft tube 2 can suck the sludge from its one open end and can discharge the sucked sludge from its other open end.

The agitator 3 is constructed such that a motor 11 is arranged outside of a bearing box 10 which is buried by mortar 9 in a concrete slab 8 of the digestion tank 1 just above the draft tube 2, as shown in FIG. 6, and such that the output shaft of the motor 11 and the shaft 12 of the screw 4 are connected through the bearing box 10.

Moreover, the shaft 12 is equipped near the sludge liquid level with a splash disc 13. Use of the splash disc 13 presents the sludge from being discharged from the upper open end of the draft tube 2 above the sludge liquid level, when the upward flow is established in the draft tube 2, and this prevents contamination of the bearing box 10 with the discharged sludge.

Here, an upper space 14 in the digestion tank 1 is filled up with the combustible digestion gas (under a pressure of about 300 mm Aq) which is composed mainly of methane gas released during the digesting step.

Figure 7:
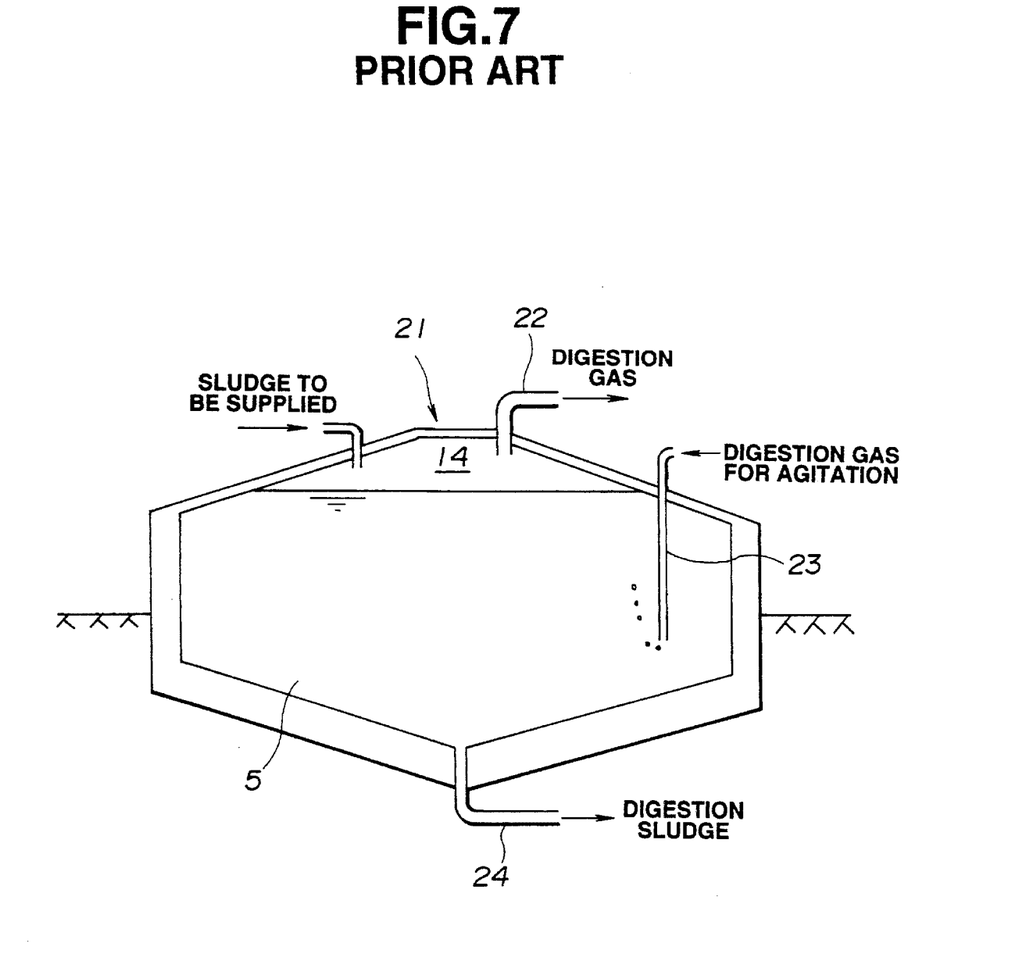
FIG. 7 is a longitudinal sectional view showing another example of a digestion tank of the prior art.

FIG. 7 is a longitudinal sectional view of the entire apparatus of another example of a digestion tank of the prior art to be used for sludge treatment in the prior art. The portions corresponding to tile aforementioned ones of FIGS. 5 and 6 are designated at the common reference numerals.

In this digestion tank 21, the digestion gas produced during the digesting step is recovered by a gas holder(not shown) through a degassing pipe 22. And then, the digesting gas is boosted in pressure by a blower (not shown) and it is injected under a predetermined pressure to the vicinity of the tank bottom via an agitating pipe 23. As a result, the sludge in the tank is agitated by digestion gas so that the organisms in the sludge may be in organized and or gas if led by the action of an anaerobe such as facultative anaerobe or methane fermentum.

The digested sludge which has been reduced, stabilized and made safe by the inorganizing and the gasifying treatments, is discharged through a digested sludge discharge pipe 24 which is disposed at the bottom center of the tank.

However, the prior art construction of the agitating apparatus, which includes the draft tube 2 erected in the digestion tank 1 and the agitator supported by a concrete slab 8 at the top of the digestion tank 1 and in which the screw 4 connected to the motor 11 of the agitator 3 is inserted into the upper open end of the draft tube 2, is a widely adopted technology. This construction presupposes that the digestion tank has been designed in advance to have a strength capable of disposing the agitator 3 in the concrete slab 8 of the top of the digestion tank 1. However, the construction has a disadvantage that it cannot be installed from the standpoint of strength on the digestion tank which has failed to take such consideration in the designed strength or on the existing digestion tank(of the type, as shown in FIG. 7).

On the other hand, the latter construction (of FIG. 7), in which the sludge 5 in the tank is agitated by injecting the digestion gas produced at the digesting step to the vicinity of the tank bottom, is inferior in agitating effect of FIG. 5, i.e., the agitating efficiency of the mechanical agitation type.

Thus, there is a tendency of increasing the need for replacing the agitating construction of the latter digestion tank 21, see FIG. 7, in which the agitation is performed by the already running gas or pump, with a mechanical agitation type. However, the following problems arise in case the agitator of FIG. 5 is installed in an existing agitation tank 21:

① The top slab of the existing digestion tank 21 may frequently have such a small thickness as to lack the strength for installing the agitator 3 or fail to maintain the strength of the concrete after one decade or two decades even if the strength was sufficient when designed. Thus, the agitator 3 cannot be safely installed on the top slab of the existing digestion tank 21.

② In this case, however, the installation could be made if the agitator 3 were placed on a strong support disposed inside or outside of the existing digestion tank 21, to bear the load and if the gas sealing of the top slab, through which the agitator 3 passes, were sufficiently devised. However, the construction is so large-sized and complicated as to raise the cost for the improvement.

③ These problems could be solved by disposing the agitator in the digestion tank. Since, however, the digestion tank is a unit for producing combustible gases, the inner construction is not easy to open and inspect. It is a common practice to perform the required maintenance work about once every five years, even if other maintenance work is needed in the interim. Thus, good maintenance cannot be sufficiently achieved, and a long down time and high cost are required, if problems should occur, which require inspections and repairs.

SUMMARY OF THE INVENTION

The present invention has an object to provide an agitating apparatus for a digestion tank, which can install an agitator of the mechanical agitation type even on existing digestion tank without overloading the top slab of the tank and can be maintained easily.

In order to achieve this object of the present invention, there is provided an agitating apparatus for a digestion tank, comprising:

a draft tube fixed upright in a digestion tank with two open ends and submerged in the sludge of the digestion tank;

a watertight pipe mounted in an outer wall of the tank just above the draft tube and having an axis aligned with an axis of the draft tube, an upper end of the watertight pipe being protruded outside of an outer wall of the digestion tank, a lower portion of the watertight pipe being protruded into an upper space of the digestion tank and a lower end of the watertight pipe being spaced from the draft tube;

a cover removably attached to the upper end of the watertight pipe;

watertight means for connecting the draft tube and the watertight pipe in watertight sealing; and an underwater agitator inserted through the watertight pipe and disposed in the draft tube, the underwater agitator being able to be extracted through the watertight pipe.

Further, in the aforementioned agitating apparatus, the watertight connecting means can be a guide pipe which is inserted from an upper opening of the watertight pipe into the watertight pipe and connected water-tightly to the upper end of the draft tube.

DESCRIPTION OF THE PREFERRED EMBODIMENTS

Figure 1:
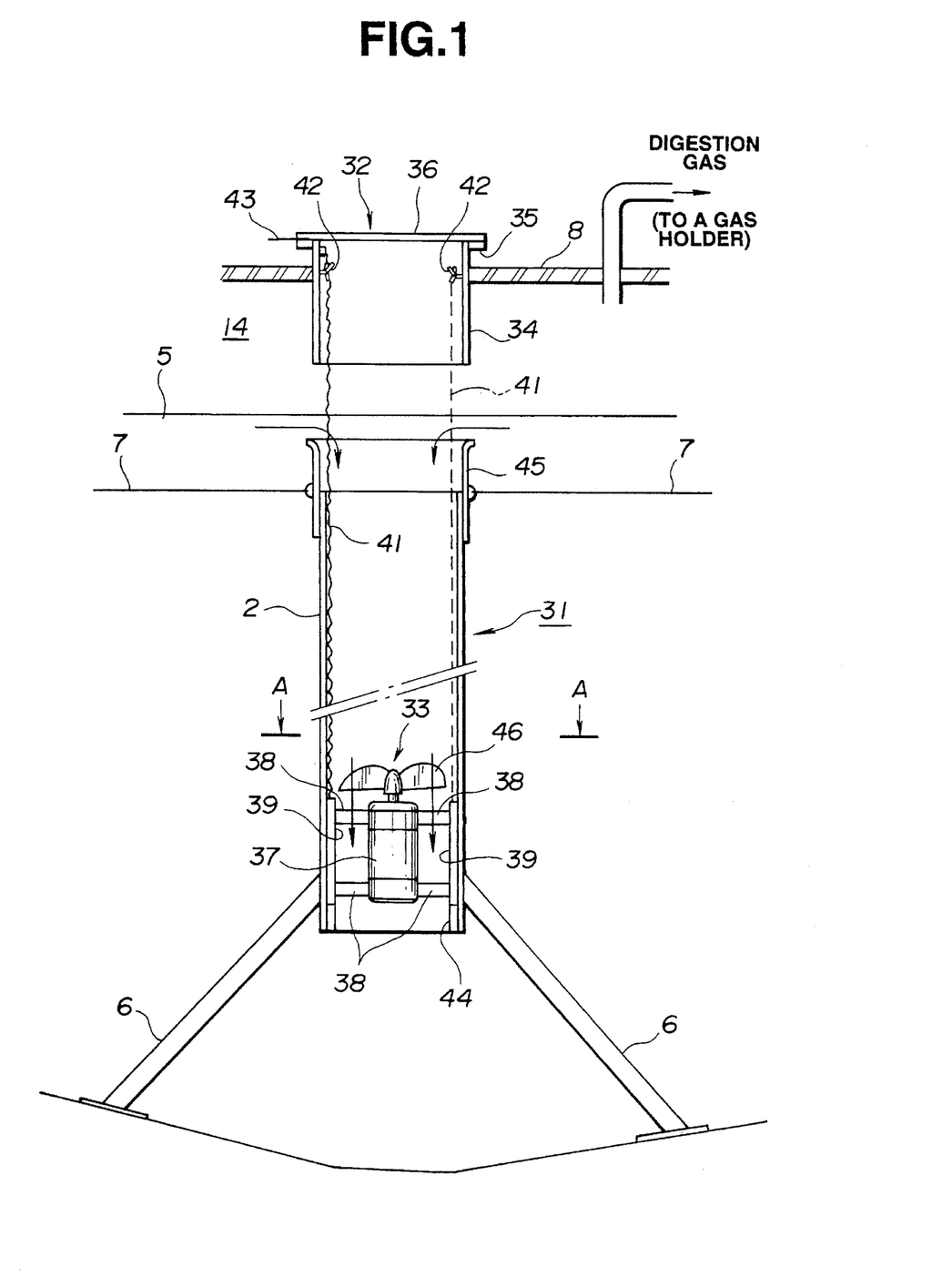
FIG. 1 is a longitudinal sectional view showing an embodiment of an agitating apparatus for a digestion tank of the present invention.
Figure 2:
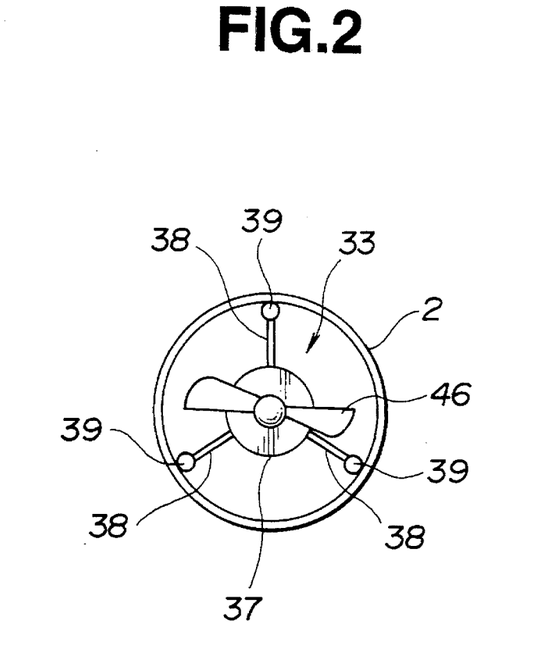
FIG. 2 is a sectional view taken along line A—A of the FIG. 1.
Figure 3:
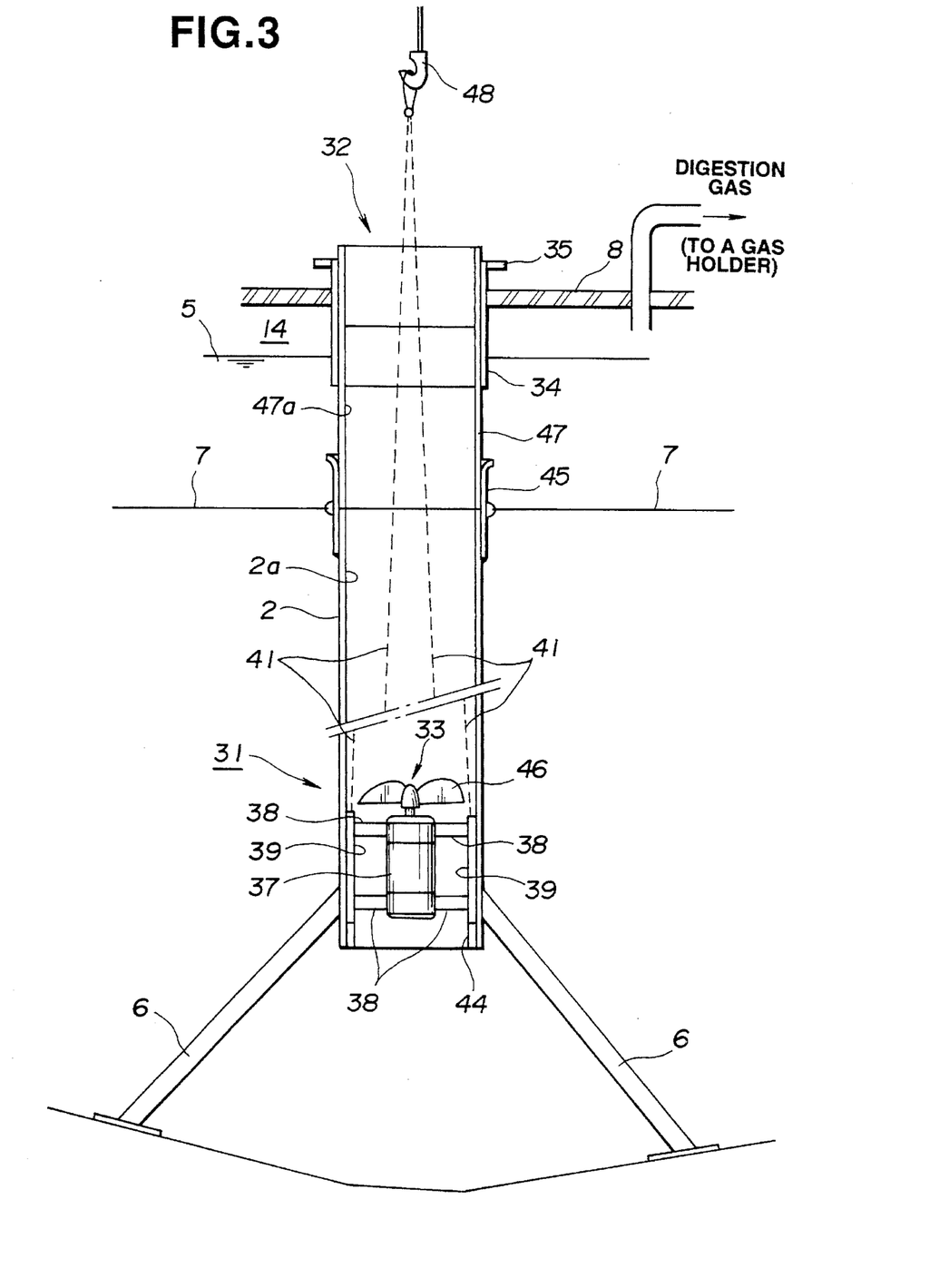
FIG. 3 is a diagram for explaining how insertion or extraction of an agitator into and out of a draft tube occurs according to the present invention.

With reference to FIG. 1, FIG. 2 and FIG. 3 an embodiment of the present invention will be given. In these figures, the identical portions are designated with common reference numerals.

In the present embodiment, an agitating apparatus 31 for a digestion tank can be installed by disposing a watertight pipe 34 to be used as an inspection hole 32 just above a draft tube 2 in a top slab 8 of the digestion tank and merely inserting an underwater agitator 33 into the draft tube 2 from the watertight pipe 34.

More specifically, the watertight pipe 34 has an internal diameter substantially equal to an external diameter of the draft tube 2 and has its lower end protruded into an upper space 14 in the digestion tank. An upper end of the watertight pipe 34 protruded outside of the top slab 8 is formed with an outward flange 35, which is covered with a cover 36. An underwater agitator 33 has a plurality of sliding rods 39.

The sliding rods 39 are integrally attached to at least three positions of a casing of a motor 37 by fixing members 38 and the sliding rods 39 extend in the axial direction of the motor. Thus, the underwater agitator 33 can vertically slide with no inclination in the draft tube 2 and the watertight pipe 34. The sliding rods 39 can be four more in number.

Attached to each of the sliding rods 39 is a fixed end of a flexible member 41 suspending the rods 39 such as wires or chains. The fixed end of each of the flexible members has another end suspended from each of a plurality of hooks 42 removably attached to the inner wall of the watertight pipe 34 providing the inspection hole 32.

A power supply cable 43 for the motor 37 is guided upward along tile inner wall of the draft tube 2 while being helically wound on one of the suspending flexible members 4I or fixed by a fixing member so that the power supply cable can be prevented from swaying or twisted during the operation of the apparatus by the sludge 5 flowing in the draft tube 2. And the power supply cable is extracted to the outside(or atmosphere) from the cover 36 through the watertight pipe 34.

In the inner circumference of the lower end portion of the draft tube 2, there is fixed a ring-shaped supporter 44 for receiving the lower ends of the individual sliding rods 39 of the underwater agitator 33. Around the outer circumference of the upper end of the draft tube 2, on the other hand, there is mounted a bell shaped mouth portion 45 which has an internal diameter equal to that of the watertight pipe 34. Stoppers, such as flat bars are attached vertically to the inner wall of the draft tube 2 to prevent the underwater agitator 33 from rotating in reaction to the screw rotation. As a result, even if the underwater agitator 33 is rotated by its own reaction, the sliding rods 39 come into abutment against the stoppers so that the agitator is prevented from rotating. When in a downward run, on the other hand, the underwater agitator can be floated by the an upward reaction. In order to prevent this, a weight capable of overcoming the floating force or a structure in which pawls are protruded outside of the sliding rods simultaneously with the power supply for starting the run, can be provided. The structure left unspecified above such as that for fixing the draft tube is similar to that of the example of the prior art.

In the agitating apparatus for the digestion tank of the present embodiment, the underwater agitator 33 and the draft tube 2 causes vibrations during the agitating run because the underwater agitator 33 has a screw 46 playing a role of a pump impeller and tile draft tube 2 plays a role of a pump casing. However, the watertight pipe 34 and the top slab 8 are less influenced by the vibration of the agitator 33 to facilitate the gas sealing between the watertight pipe 34 and the top slab 8 because the watertight pipe 34, which provides the inspection hole 32, and the draft tube 2 are spaced from each other and because the agitator 33 and watertight pipe 34 are connected merely through the flexible members 41. As a result, a downward or upward intensive flow can be established in the draft tube 2 as well as in the agitator of the prior art so that the sludge in the digestion tank of a large capacity can be efficiently agitated.

When the underwater agitator 33 is to be inspected, as shown in FIG. 3, the water level in the digestion tank is raised at first to seal the lower end opening of the sealing pipe 34 which is the inspection hole 32 with the water. Next, the cover 36 of the inspection hole 32 is removed, and a guide pipe 47 for connecting the watertight pipe 34 and the draft tube 2 to seal them from the space in the digestion tank is downward inserted into the watertight pipe 34, as shown in FIG. 3. Before the insertion preparation work, the power supply cable 43, the individual suspending flexible members 41 and the individual hooks 42 are removed to leave no obstruction at the time of taking out the underwater agitator. And then, the individual suspending flexible members 41 are hooked by a crane hook 48, and the underwater agitator 33 is taken outside. The guide pipe 47 is set to make its inner circumference 47a coextensive with the inner circumference 2a of the draft tube 2 when these two are to be connected. As a result, the watertight pipe 34 and the draft tube 2 are connected by the guide pipe 47 to form a single tube extending from the draft tube 2 to the watertight pipe 34 without steps, on the internal faces. Thus, the underwater agitator 33 can be smoothly taken out without interference or collision against a step. The resetting of the underwater agitator 33 is done by following the steps reverse to those mentioned above.

Thus, the agitating apparatus for the digestion tank of the present embodiment can be installed by disposing the watertight pipe 34 to work as the inspection hole 32 in the top slab 8 of the digestion tank just above the draft tube 2 and by inserting the underwater agitator 33 into the draft tube 2 from the watertight pipe 34. As a result, the agitator can be simply installed and the load upon the top slab 8 of the digestion tank can be reduced. Thus, the present invention can be applied even to existing digestion tanks which have a thin or fragile top slab.

Since, moreover, the inspection hole 32 is exemplified by the watertight pipe 34 which protrudes into the upper space 14 in the digestion tank for the sealing operation, the inspection hole 32 can be sealed with the sludge 5 in the digestion tank. As a result, the inside can be easily inspected to facilitate maintenance even when combustible digestion gas fills the upper space 14 in the digestion tank.

Figure 4:
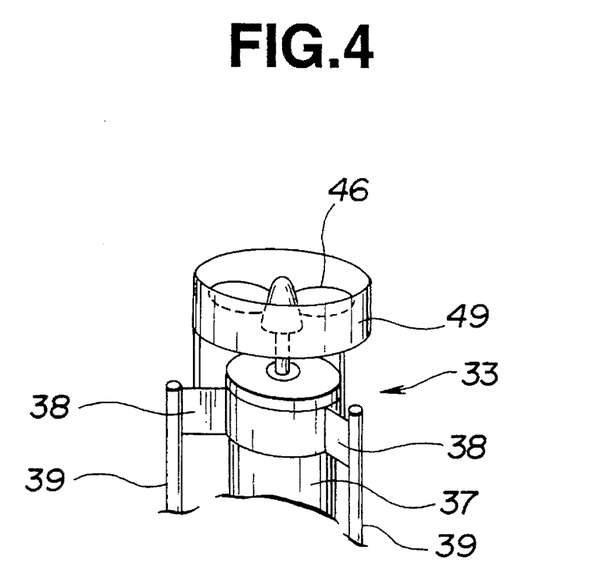
FIG. 4 is a perspective view showing another embodiment of the agitating apparatus for the tank of the present invention.

Incidentally, the foregoing embodiment exemplifying an underwater agitator 33 in the draft tube 2 such that the screw 46 is disposed above the motor 37. In order to prevent the suspending flexible members 41 and the power supply cable 43 from being wound by the screw 46, however, the setting can be made such that the screw 46 is disposed below the motor 37 or such that the screw 46 is surrounded by a protecting casing 49 for a higher efficiency, as shown in FIG. 4.

As have been described hereinbefore, according to the present invention, the agitating apparatus can be installed merely by inserting the underwater agitator into the draft tube from the inspection hole which is formed in the outer wall of the digestion tank just above the draft tube. As a result, the agitator can be easily installed to reduce the burden upon the outer tank wall just above the draft tube. Thus, the present invention can also be applied to existing digestion tanks which have a thin or fragile top slab.

Since, however, the inspection hole is exemplified by a watertight sealing pipe 34 projected into the upper space in the digestion tank, it can be sealed up with the sludge in the digestion tank. As a result, the inside can easily be inspected to facilitate maintenance even when combustible digestion gas fills up the upper space in the digestion tank.

According to the present invention, furthermore, the structure of the inspection hole is made so a the guide pipe is inserted into the watertight pipe function as the inspection hole by sealing the watertight pipe and the draft tube from the space in tile digestion tank by use of the guide pipe. As the result, the underwater agitator can be introduced into or extracted from the draft tube, via a single pipe extending from the draft tube to the inspection hole which is formed by inserting the guide pipe. Thus, the underwater agitator can be smoothly inserted into and extracted from the draft tube.

According to the present invention, furthermore, the inner wall of the guide pipe is made coextensive with the inner wall of the draft tube to form a uniform inner wall, so that no step is formed on the single tube which is formed from the draft tube to the inspection hole by inserting the guide pipe. As a result, no interference can be established between the underwater agitator and the draft tube, when the former is introduced into or extracted from the latter, to prevent an accident which might otherwise be caused when the underwater agitator collides with the step.

What is claimed is:

1. Agitating apparatus for a digestion tank, comprising:
   a draft tube having two open end portions, the draft tube being fixed in an upright direction in a digestion tank, such that one of the open end portions thereof is submerged in sludge in the digestion tank;
   a watertight pipe mounted in an outer wall of the digestion tank and above said draft tube, said watertight pipe having an axis which is aligned with an axis of said draft tube, an upper end of said watertight pipe protruding outside of the outer wall of the digestion tank, a lower portion of said watertight pipe protruding into an upper space of the digestion tank and a lower end of said watertight pipe being spaced apart from the draft tube;
   a cover removably attached to the upper end of said watertight pipe;
   connecting means coupled between said draft tube and said lower end of said watertight pipe for connecting said draft tube and said lower end of said watertight pipe in a water-tight manner; and
   an underwater agitator inserted through said watertight pipe and disposed in said draft tube, said underwater agitator being extractable from the draft tube through said watertight pipe.

2. The agitating apparatus of claim 1, wherein said connecting means includes a guide pipe insertable from an upper opening of said watertight pipe into said watertight pipe, said guide pipe being connected to provide a watertight connection at an upper end of said draft tube.

3. The agitating apparatus of claim 2, wherein said guide pipe has an inner diameter that is equal to an inner diameter of said draft tube.

4. The agitating apparatus of claim 1, wherein said underwater agitator includes a plurality of sliding rods for sliding along an inner wall of said draft tube.

5. The agitating apparatus of claim 4, further comprising support means mounted on an inner wall of said draft tube for supporting said underwater agitator by placing said sliding rods on said support means.

6. The agitating apparatus of claim 1, further comprising:
   a plurality of hooks removably attached to an inner wall of said watertight pipe; and
   flexible members connecting said underwater agitator and said plurality of hooks.

7. The agitating apparatus of claim 6, wherein said flexible members comprise chains.

8. The agitating apparatus of claim 6, wherein said flexible members comprise wires.

9. The agitating apparatus of claim 1, further comprising a bell shaped mouth portion mounted on an outer wall of said draft tube and projected from an upper end of said draft tube.

10. The agitating apparatus of claim 9, wherein said bell shaped mouth portion has an inner diameter that is equal to an inner diameter of said watertight pipe.

* * * * *

UNITED STATES PATENT AND TRADEMARK OFFICE
CERTIFICATE OF CORRECTION

PATENT NO. : 5,505,541
DATED : April 9, 1996
INVENTOR(S) : KIHARA, YASUHIKO

It is certified that error appears in the above-indentified patent and that said Letters Patent is hereby corrected as shown below:

The title page, showing an illustrative figure, should be deleted and substitute therefor the attached title page.

Delete Figure 1, and substitute therefor the Figure, consisting of Figure 1, as shwon on the attached page:

United States Patent [19]
Kihara

[11] Patent Number: 5,505,541
[45] Date of Patent: Apr. 9, 1996

[54] STRUCTURE FOR MOUNTING AN AGITATING APPARATUS FOR A DIGESTION TANK

[75] Inventor: Yasuhiko Kihara, Kawasaki, Japan

[73] Assignee: NKK Corporation, Tokyo, Japan

[21] Appl. No.: 312,459

[22] Filed: Sep. 26, 1994

[30] Foreign Application Priority Data

Apr. 28, 1994 [JP] Japan .................................. 6-091937

[51] Int. Cl.[6] .................................................. B01F 5/12
[52] U.S. Cl. ........................................ 366/264; 366/286
[58] Field of Search .................................. 366/262–264,
366/266, 285, 286, 261, 330.1, 347; 261/84,
91, 119.1; 415/221

[56] References Cited

U.S. PATENT DOCUMENTS

| | | | |
|---|---|---|---|
| 2,090,384 | 8/1937 | Durdin, III | 261/91 X |
| 2,186,371 | 1/1940 | Durdin, Jr. | 261/91 X |
| 2,647,733 | 8/1953 | Knowles et al. | 366/286 |
| 4,030,859 | 6/1977 | Henegar | 261/91 X |

FOREIGN PATENT DOCUMENTS

544784  8/1957  Canada .......................... 366/262

Primary Examiner—Charles E. Cooley
Attorney, Agent, or Firm—Frishauf, Holtz, Goodman, Langer & Chick

[57] ABSTRACT

An agitating apparatus for a digestion tank includes a draft tube having two open ends. The draft tube is fixed in an upright direction in a digestion tank such that one open end thereof is submerged in sludge in the digestion tank. A watertight pipe is mounted in an outer wall of the digestion tank to be just above the draft tube such that the watertight pipe has an axis thereof aligned with an axis of the draft tube. An upper end of the watertight pipe protrudes outside of the outer wall of the digestion tank, a lower portion of the watertight pipe protrudes into an upper space of the digestion tank and a lower end of the watertight pipe is spaced apart from the draft tube. The agitating apparatus also includes a cover removably attached to the upper end of the watertight pipe. A watertight connection connects the draft tube and the watertight pipe to each other. An underwater agitator is inserted through the watertight pipe and is disposed in the draft tube. The underwater agitator is extractable through the watertight pipe.

10 Claims, 6 Drawing Sheets

FIG.1

UNITED STATES PATENT AND TRADEMARK OFFICE
CERTIFICATE OF CORRECTION

PATENT NO. : 5,505,541
DATED : April 9, 1996
INVENTOR(S) : KIHARA, Yasuhiko

It is certified that error appears in the above-indentified patent and that said Letters Patent is hereby corrected as shown below:

Title page, Item [56] References Cited, under "FOREIGN PATENT DOCUMENTS", insert
--59-46654  11/1984  Japan--.

In the Drawings, in FIG.1, "A" (in both occurrences) should be --II--; and a dashed section line should be added (see attached corrected drawing).

Column 1, line 44, "presents" should be --prevents--;
line 47, "this" should be --thus--;
last line, "in organized" should be --inorganized--;
same line, "gas if led" should be --gasified--.

Column 2, line 63, "tank" should be --tanks--.

Column 3, line 31, "line A—A of the" should be --line II—II of--;
line 58, "and" should be --by--.

UNITED STATES PATENT AND TRADEMARK OFFICE
CERTIFICATE OF CORRECTION

PATENT NO. : 5,505,541
DATED : April 9, 1996
INVENTOR(S) : KIHARA, Yasuhiko

It is certified that error appears in the above-indentified patent and that said Letters Patent is hereby corrected as shown below:

Column 4, line 4, "tile" should be --the--;
          line 17, before "twisted" insert --being--;
          line 62, "sealing" should be --watertight--.

Column 5, line 34, "exemplifying" should be --exemplifies--;
          line 59, "so a the guide pipe" should --so that a guide pipe--;
          line 60, "function" should be --functioning--.

Signed and Sealed this

Twelfth Day of August, 1997

Attest:

BRUCE LEHMAN

Attesting Officer     Commissioner of Patents and Trademarks